United States Patent
Muraishi

(10) Patent No.: US 7,534,624 B2
(45) Date of Patent: May 19, 2009

(54) METHOD AND APPARATUS FOR ASSAY IN UTILIZING ATTENUATED TOTAL REFLECTION, AND SAMPLE IMMOBILIZING DEVICE

(75) Inventor: Katsuaki Muraishi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 383 days.

(21) Appl. No.: 11/230,504

(22) Filed: Sep. 21, 2005

(65) Prior Publication Data

US 2007/0231924 A1   Oct. 4, 2007

(30) Foreign Application Priority Data

Sep. 21, 2004   (JP) .............. 2004-272958

(51) Int. Cl.
  *G01N 33/543*   (2006.01)
  *G01N 33/551*   (2006.01)

(52) U.S. Cl. ............ 436/518; 422/56; 422/58; 422/82.11; 435/288.5; 435/288.7; 435/808; 436/164; 436/514; 436/524; 436/525; 436/805

(58) Field of Classification Search ............. None
See application file for complete search history.

(56) References Cited

U.S. PATENT DOCUMENTS

| 5,313,264 A | 5/1994 | Ivarsson et al. |
| 5,725,831 A | 3/1998 | Reichler et al. |
| 5,822,073 A | 10/1998 | Yee et al. |
| 2002/0149775 A1* | 10/2002 | Mori et al. ........... 356/445 |

FOREIGN PATENT DOCUMENTS

| CA | 2215561 A1 | 9/1997 |
| EP | 1 251 345 A1 | 10/2002 |
| EP | 1 324 019 A1 | 7/2003 |
| JP | 4-501462 A | 3/1992 |
| JP | 05-005734 A | 1/1993 |
| JP | 6-167443 A | 6/1994 |
| JP | 7-265100 A | 10/1995 |
| JP | 10-150975 A | 6/1998 |

* cited by examiner

*Primary Examiner*—Christopher L Chin
(74) *Attorney, Agent, or Firm*—Sughrue Mion, PLLC

(57) ABSTRACT

A sensor unit for assay in utilizing surface plasmon resonance (SPR) includes a dielectric prism. Metal film has a light entrance surface fitted on the prism, and a sensing surface reverse to the light entrance surface. The sensing surface is adapted to causing interaction between ligand of ligand liquid and analyte liquid. An optical assay unit includes a light source, optical system and photo detector. A flow channel includes the sensing surface positioned inside. In an immobilizing stage, the ligand is immobilized on the sensing surface by introducing the ligand liquid to the flow channel. Evaporation retardant is introduced to the flow channel, and prevents drying of the ligand. The evaporation retardant is removed from the flow channel after transfer of the sensor unit from the immobilizing stage to an assay stage. The analyte liquid is introduced to the flow channel, to assay the interaction.

10 Claims, 5 Drawing Sheets

METHOD AND APPARATUS FOR ASSAY IN UTILIZING ATTENUATED TOTAL REFLECTION, AND SAMPLE IMMOBILIZING DEVICE

BACKGROUND OF THE INVENTION

1. Field of the Invention

The present invention relates to a method and apparatus for assay in utilizing attenuated total reflection, and a sample immobilizing device. More particularly, the present invention relates to a method and apparatus for assay in utilizing attenuated total reflection, and a sample immobilizing device, in which a sample can be assayed reliably by keeping fluidity in a flow channel according to a surface plasmon resonance (SPR) biosensor system, and also a sample immobilizing device.

2. Description Related to the Prior Art

An assay apparatus in utilizing attenuated total reflection for assaying a sample is known in the field of the biosensor. A thin film, or metal film, is formed on a transparent dielectric medium. One surface of the metal film is a sensing surface where reaction of a sample is occurs. Another surface of the metal film is a light entrance surface where light is applied by satisfying a condition of total reflection. The reaction is detected to assay the sample according to attenuation of the reflected light from the light entrance surface. U.S. Pat. No. 5,313,264 (corresponding to JP-A 4-501462) discloses a surface plasmon resonance (SPR) sensor as a typical example for this assay.

In a metal, free electrons vibrate to generate the compressional wave called a plasma wave. Surface plasmon is a term to mean the compressional wave created on the surface of the metal and included in plasmon as quantized expression of the compressional wave. The surface plasmon travels along the surface of the metal. The surface plasmon resonance (SPR) assay apparatus is constructed to detect surface plasmon resonance- created on the sensing surface which is a first surface of the metal film.

Light for detection is applied to a light entrance surface of the metal film that is back to the sensing surface so that the total reflection condition is satisfied, namely at an angle of incidence equal to or more than a critical angle. In addition to the total reflection created on the light entrance surface, a small component of the light passes through the metal film without reflection, and penetrates to the sensing surface. A wave of the penetrating component is called an evanescent wave. Surface plasmon resonance (SPR) is created as when frequency of the evanescent wave coincides with that of the surface plasmon. In response to this, intensity of the reflected light attenuates remarkably. In the assay apparatus, the attenuation in the reflected light reflected by the light entrance surface is detected, to recognize creation of the SPR on the sensing surface.

The angle of incidence, namely resonance angle of the light to generate the SPR depends on the refraction index of the transmission medium transmitting evanescent wave and surface plasmon. In other words, a change in the resonance angle to create SPR changes in response to a change in the refraction index of the transmission medium. The substance contacting the sensing surface is a transmission medium transmitting the evanescent wave and surface plasmon. If binding or separation between two molecules occurs on the sensing surface, the resonance angle changes because of a change in the refraction index of the transmission medium. In the SPR system, the change in the refraction index is detected, to measure interaction of molecules.

The assay apparatus can be used for various kinds of studies in a biochemical field or the like, for example to study interaction of protein, DNA and various biochemical substances, and to select candidate drugs by screening. It is possible to use one of two substances as a ligand and another one of them as an analyte if those have bioaffinity. For the purpose of screening, protein as biomaterial is used as ligand. Candidate drugs are discretely used as analyte, and contacted with the ligand on the sensing surface, to study interaction.

JP-A 6-167443 and U.S. Pat. No. 5,822,073 disclose an SPR assay apparatus in which an optical system of Kretschmann configuration is used for incidence of light to the metal film. According to the Kretschmann configuration, the light entrance surface of the metal film is fitted on a prism, which condenses light and directs the light to the light entrance surface in a manner conditioned for total reflection. A sample or ligand is immobilized on the sensing surface. A flow channel is formed to have the sensing surface inside, and causes analyte liquid to flow. The analyte liquid is introduced in the flow channel to flow, and is caused to contact the ligand. Interaction between the analyte liquid and the ligand is assayed by detecting surface plasmon resonance created during the reaction.

JP-A 6-167443 discloses an assay stage disposed in the apparatus casing and having a prism and a flow channel. A sensor of a chip type according to the SPR system is placed on the assay stage, the sensor including a glass base board which is dielectric and transparent, and metal film overlaid thereon. The sensor of the chip type is secured to the apparatus casing removably, and positioned so as to set the sensor surface inside the flow channel of the casing, and set the light entrance surface on the prism. Prior to the assay, it is necessary in a pre-treatment to immobilize ligand on metal film of the sensor of the chip type. This is ligand immobilization. According to the SPR system of JP-A 6-167443, the sensor of the chip type is kept mounted on the assay stage.

At first before the assay, the sensing surface of the sensor of the chip type appears externally. A portion of the flow channel at the sensing surface is open. When the sensor of the chip type is mounted on the assay stage, the sensing surface covers and encloses the open portion of the flow channel. This enables introduction of liquid to the flow channel. Ligand liquid is introduced to the flow channel, and ligand is immobilized. After this, analyte liquid is introduced before assay is made.

However, there is a problem in the above assay by use of the sensor of the chip type. The assay process directly follows the immobilization for one sensor. Efficiency or throughput in the operation of the assay system cannot be raised if the immobilization is made for a plurality of the sensor of the chip type. The same assay stage is used for either of the immobilization and the assay process. The assay process would not be conducted during the immobilization for next sample. The immobilization has a low speed of a rate-determining level defining the low speed of the entire assay system even though the assay process is possible in a quick manner. Suggestions have been made for improving efficiency in the immobilization which requires much more time than the assay process.

It is conceivable to raise throughput of the assay by the immobilization for plural sensors together, and by serially assaying plural sensors after the immobilization. The sensor are mounted on the assay stage and subjected to the immobilization. Each one of the sensors after the immobilization is removed from the assay stage. Other sensors are then mounted on the assay stage for the immobilization. By repeating such a sequence, the immobilization is collected for the plural sensors. After this, the sensors after the immobilization are mounted on the assay stage one after another, and subjected to the assay. Thus, the immobilization can be completed together before the assay in the collective manner irrespective of time required by the immobilization. Improvement in the throughput of the assay might be expected.

If the sensor of the chip type is removed from the assay stage, the sensing surface dries by volatilization because uncovered externally. The sensing surface cannot be kept wet. Molecules or other substances as ligand, for example protein, are likely to degrade by drying in relation to initial characteristic, for example properties as enzymes and affinity for binding with other substances. It is impossible to recognize the properties accurately if drying proceeds after the immobilization until the assay.

Even if a substance does not change functionally upon drying, the substance comes in a state not returning to an initial state even when liquid is abruptly provided. No reaction will occur upon the start of the onset. Namely, a signal output is unstable. This lengthens the time of assay, because sufficient time is required for stability in the output signal.

No known technique solves those problems in the assay due to temporary drying of ligand after the immobilization until the onset of assay.

SUMMARY OF THE INVENTION

In view of the foregoing problems, an object of the present invention is to provide a method and apparatus for assay in utilizing attenuated total reflection, and a sample immobilizing device, in which a sample can be assayed reliably by keeping fluidity in a flow channel according to a surface plasmon resonance (SPR) biosensor system, and also a sample immobilizing device.

In order to achieve the above and other objects and advantages of this invention, an assay method in utilizing attenuated total reflection by use of at least one sensor unit and an optical assay unit, wherein the sensor unit includes a transparent dielectric medium, and thin film having a light entrance surface and a sensing surface reverse to the light entrance surface, the light entrance surface being an interface in connection with the dielectric medium, and the sensing surface being adapted to causing interaction between ligand of ligand liquid and analyte liquid, wherein the optical assay unit applies illuminating light through the dielectric medium to the light entrance surface in such a form as to satisfy a condition of total reflection, and assays interaction between the ligand and the analyte liquid by detecting attenuation of the illuminating light reflected by the light entrance surface. In the assay method, the sensor unit includes a flow channel block having a flow channel for causing the ligand liquid and the analyte liquid to flow to the sensing surface. There is a step of, in an immobilizing stage, immobilizing the ligand on the sensing surface by introducing the ligand liquid to the flow channel. Evaporation retardant is introduced to the flow channel, for preventing drying of the ligand. The evaporation retardant is removed from the flow channel after transfer of the sensor unit from the immobilizing stage to an assay stage. The analyte liquid is introduced to the flow channel, to assay the interaction.

Preferably, the at least one sensor unit is plural sensor units, and the immobilizing step and the retardant introducing step are conducted for the plural sensor units together with one another in the immobilizing stage. Thereafter, the sensor units are provided to the assay stage discretely, to conduct the retardant removing step and the assaying step.

Furthermore, liquid buffer is introduced to the flow channel, to discharge the analyte liquid from the flow channel by substitution, and to release the analyte liquid from the ligand.

Preferably, the flow channel keeps the evaporation retardant contained after introduction thereof and until setting on the assay stage.

Preferably, in the assay stage, additional liquid is introduced to the flow channel with the evaporation retardant left to stand therein, and the additional liquid is caused to discharge the evaporation retardant from the flow channel by substitution.

Preferably, the additional liquid is buffer.

Preferably, the evaporation retardant is any one of liquid buffer, solution of a physiological salt, and pure water.

Preferably, the flow channel has a liquid orifice formed to open externally in the sensor unit, and a lid closes the liquid orifice in an openable manner. In at least one of the retardant introducing step and the retardant discharging step, a pipette is used, and operates while the lid is open to introduce the evaporation retardant to the flow channel, or to remove the evaporation retardant from the flow channel by suction.

Furthermore, liquid is stored in a liquid reservoir to be introduced to the flow channel. The pipette is supplied with the liquid from the liquid reservoir by suction. The pipette is moved to position the pipette on the sensor unit. The flow channel is supplied with the liquid from the pipette in dispensation.

Furthermore, the sensor unit is moved substantially vertically from a sensor holder, to pick up the sensor unit. The sensor unit is moved in a first horizontal direction, to position the sensor unit on the optical assay unit. The pipette supplies the sensor unit with the liquid, and the optical assay unit operates for the assay.

Furthermore, the sensor holder is moved in a second horizontal direction, to set the sensor unit in a position for the picking up.

Furthermore, in the immobilizing stage, washing buffer is introduced to the flow channel after immobilizing by introducing the ligand liquid and before introduction of the evaporation retardant.

Furthermore, blocking liquid for blocking is introduced to the flow channel after immobilizing by introducing the ligand liquid and before introduction of the evaporation retardant.

Furthermore, in the immobilizing stage, buffer for wetting the sensing surface is introduced to the flow channel before the ligand liquid is introduced.

Furthermore, in the immobilizing stage, activating liquid for activation is introduced to the flow channel before the ligand liquid is introduced.

Preferably, the thin film is metal film, and the sensor unit is a surface plasmon resonance sensor for generating surface plasmon resonance on the sensing surface.

In one aspect of the invention, an assay apparatus for assay in utilizing attenuated total reflection is provided, having at least one sensor unit, including a transparent dielectric medium, and thin film having a light entrance surface and a sensing surface reverse to the light entrance surface, the light entrance surface being fitted on the dielectric medium, and the sensing surface being adapted to causing interaction between ligand of ligand liquid and analyte liquid. An optical assay unit applies illuminating light through the dielectric medium to the light entrance surface in such an orientation as to satisfy a condition of total reflection, and detects the illuminating light reflected by the light entrance surface during the interaction of the ligand and the analyte liquid. The assay apparatus includes a flow channel, formed in the sensor unit, and including the sensing surface positioned inside. An immobilizing stage immobilizes the ligand on the sensing surface by introducing the ligand liquid to the flow channel. A liquid dispenser introduces evaporation retardant to the flow channel for preventing drying of the ligand. A liquid remover removes the evaporation retardant from the flow channel after transfer of the sensor unit from the immobilizing stage thereto. An assay stage has the liquid remover in operation, for introducing the analyte liquid to the flow channel, to assay the interaction.

Furthermore, a first casing has the immobilizing stage. A second casing is separate from the first casing, and has the assay stage.

Furthermore, a lid closes a liquid orifice of the flow channel in an openable manner, the liquid orifice being formed to open externally in the sensor unit. At least one of the liquid dispenser and the liquid remover is at least one pipette, and operates while the lid is open to introduce the evaporation retardant to the flow channel, or to remove the evaporation retardant from the flow channel by suction.

In another aspect of the invention, a sample immobilizing device for assay in utilizing attenuated total reflection by use of at least one sensor unit and an optical assay unit is provided. The sensor unit includes a transparent dielectric medium, and thin film having a light entrance surface and a sensing surface reverse to the light entrance surface, the light entrance surface being fitted on the dielectric medium, and the sensing surface being adapted to causing interaction between ligand of ligand liquid and analyte liquid, wherein the optical assay unit applies illuminating light through the dielectric medium to the light entrance surface in such an orientation as to satisfy a condition of total reflection, and detects the illuminating light reflected by the light entrance surface during the interaction of the ligand and the analyte liquid. The sample immobilizing device includes a flow channel, formed in the sensor unit, and including the sensing surface positioned inside. There is a setting space for placing plural sensor units that are the sensor unit in a serially arranged state. A ligand liquid dispenser introduces the ligand liquid to the flow channel in the plural sensor units on the setting space.

Preferably, the sensor unit includes plural sensor cells each of which includes the sensing surface and the flow channel.

Furthermore, a liquid reservoir is positioned in an accessible manner by the pipette, for storing the evaporation retardant.

According to the present invention, a sample can be assayed reliably by keeping fluidity in a flow channel, because drying can be prevented by means of the evaporation retardant.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
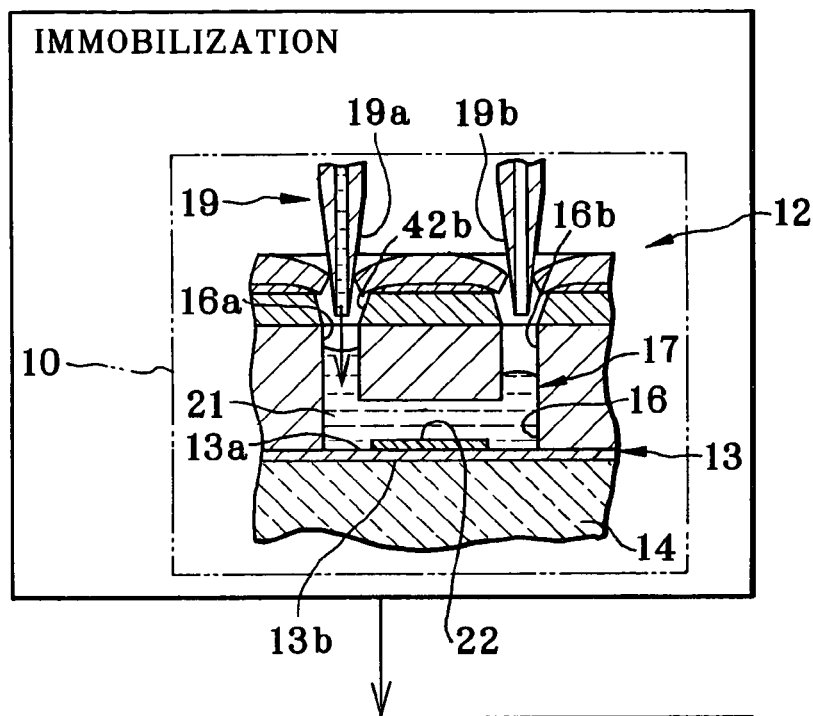
FIG. 1A is a cross section, partially broken, illustrating a sensor unit in an assay apparatus according to the SPR sensing and in a sample immobilizing process.
Figure 1B:
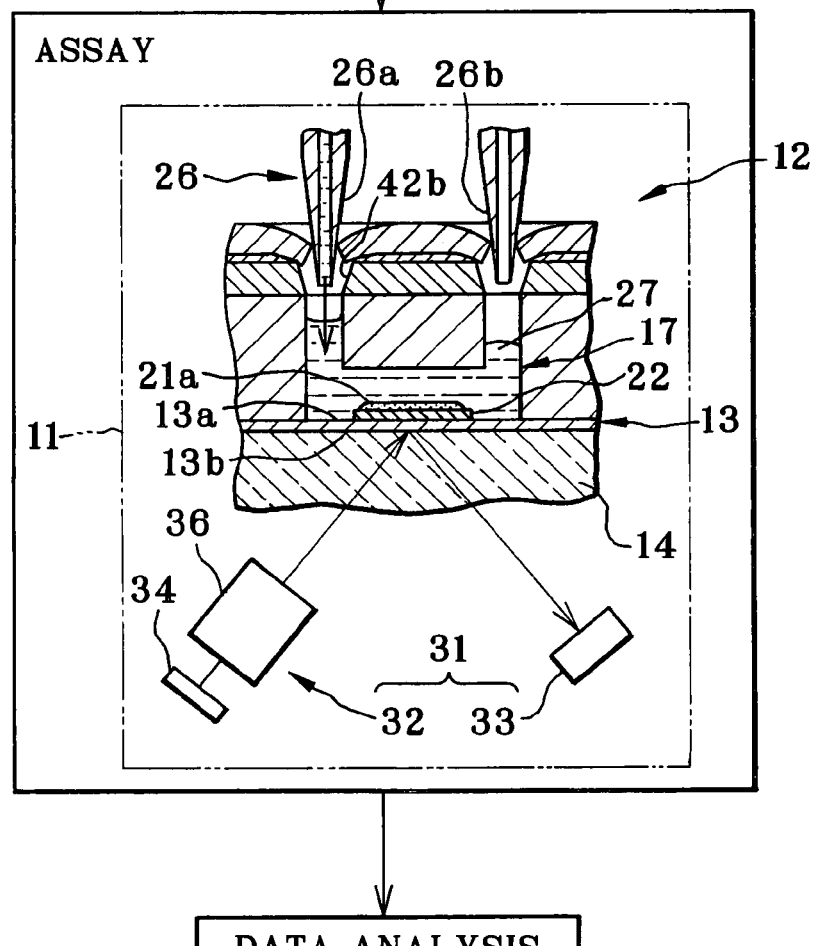
FIG. 1B is an explanatory view in cross section, illustrating the assay apparatus in an assay process and data analyzing process.
Figure 4:
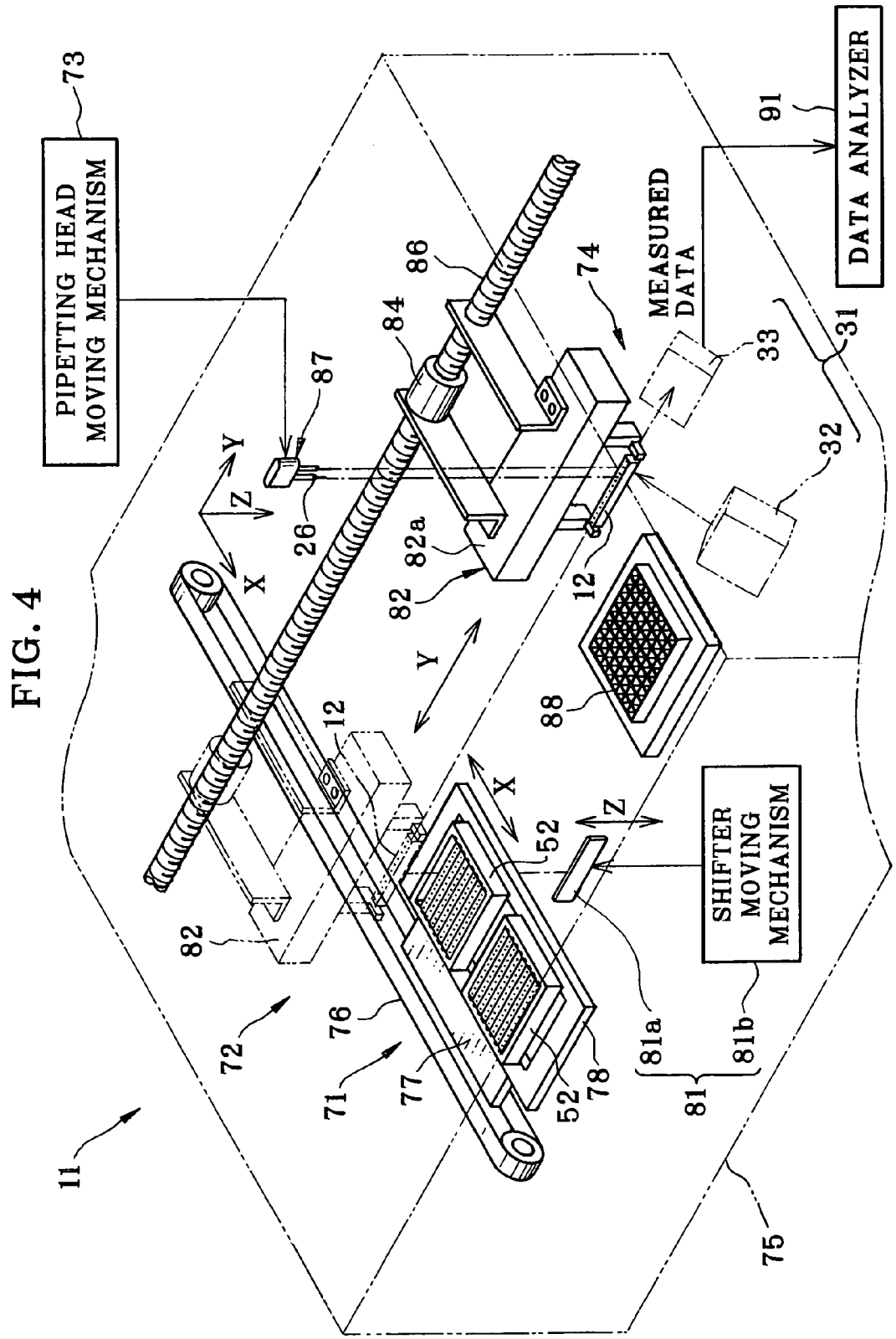
FIG. 4 is a perspective view illustrating the assay apparatus.
Figure 5:
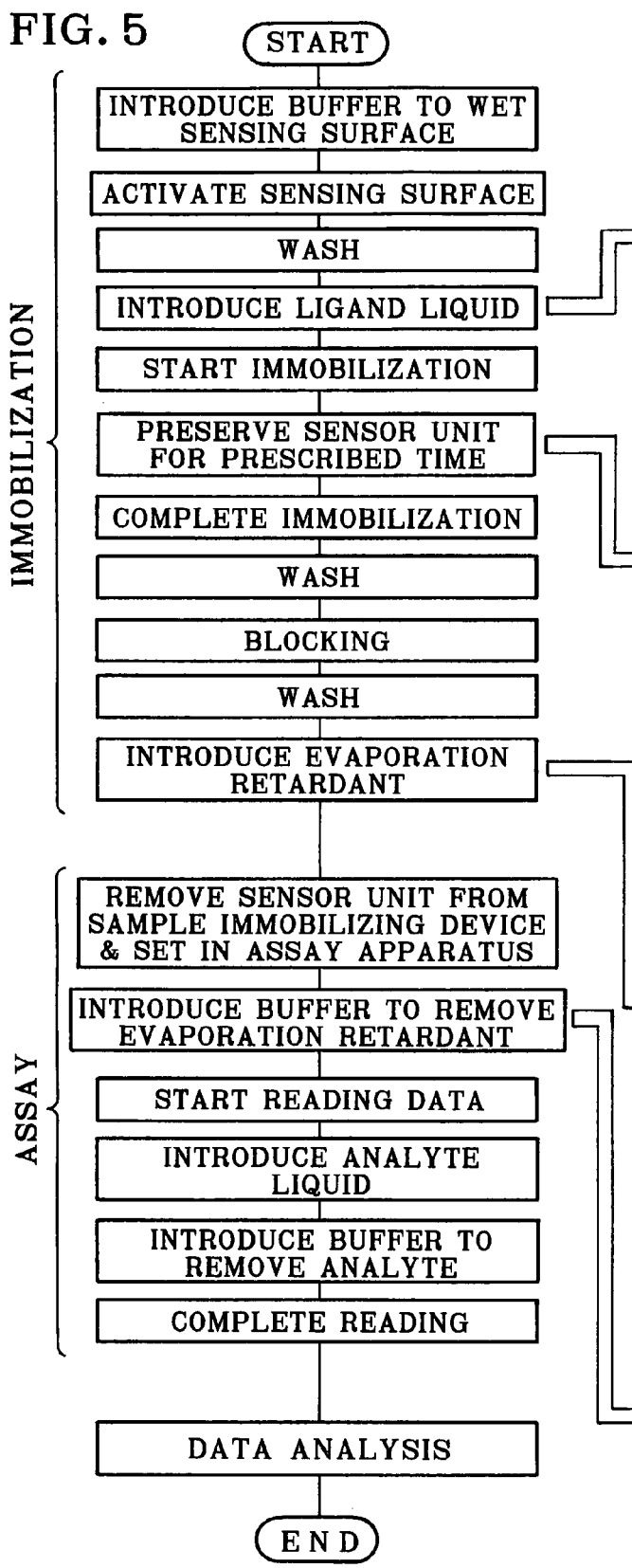
FIG. 5 is a flow chart illustrating assay according to the invention.
Figure 5A:
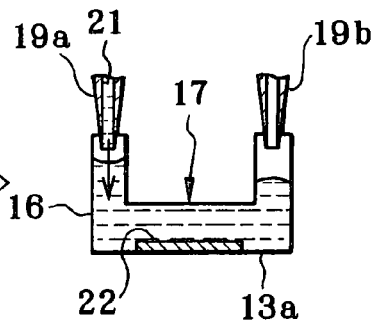
FIG. 5A is a cross section illustrating introduction of ligand liquid.
Figure 5B:
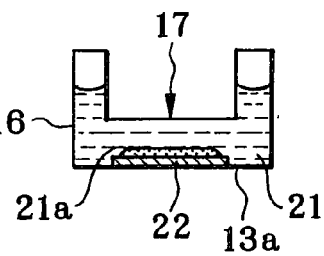
FIG. 5B is a cross section illustrating immobilization of ligand.
Figure 5C:
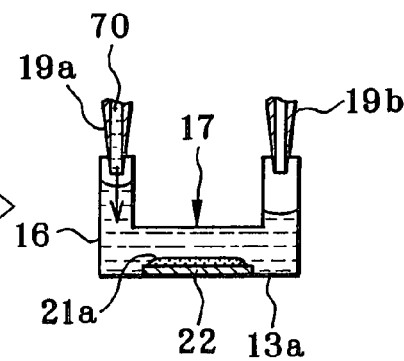
FIG. 5C is a cross section illustrating introduction of evaporation retardant.
Figure 5D:
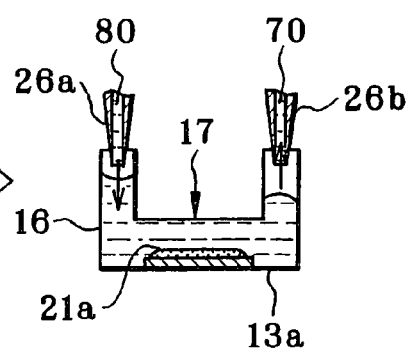
FIG. 5D is a cross section illustrating removal of the evaporation retardant by means of buffer.

In FIGS. 1A and 1B, a system for measuring or assay according to SPR (surface plasmon resonance) is illustrated. A sequence of the assay system is constituted by three processes which are a sample immobilizing process, assay process and data analyzing process. The assay system includes a sample immobilizing device 10, an assay apparatus 11, and a data analyzer 91, which is illustrated in FIG. 4.

A surface plasmon resonance (SPR) biosensor is used as a sensor unit 12 for assay. The sensor unit 12 includes a metal film 13, a prism 14 and a flow channel 16. A first surface of the metal film 13 is a sensing surface 13a where surface plasmon resonance is created. A second surface of the metal film 13 is a light entrance surface 13b where the prism 14 is fitted. The flow channel 16 extends along the sensing surface 13a, and causes ligand and analyte as liquids to flow.

An example of material for the metal film 13 is gold (Au). A thickness of the metal film 13 is 50 nm. The thickness can be changed for the suitability in view of the material of the metal film 13, a wavelength of light to be applied, and the like. The prism 14 is a transparent dielectric medium on which the metal film 13 is formed, and also is an optical element for condensing light toward the light entrance surface 13b for satisfying the condition of the total reflection. The flow channel 16 is a U-shaped conduit, and has an entrance liquid orifice 16a and an exit liquid orifice 16b. A diameter of the flow channel 16 is approximately 1 mm. An interval between the entrance liquid orifice 16a and the exit liquid orifice 16b is approximately 10 mm.

A lower side of the flow channel 16 is open initially, but closed in a firmly enclosed manner by covering of the sensing surface 13a. Sensor cells 17 are constituted by combinations of the flow channel 16 and the sensing surface 13a. The sensor unit 12 includes a plurality of the sensor cells 17. See FIG. 2. This will be described later in detail.

The immobilizing process is a binding step of ligand on the sensing surface 13a. At first, the sensor unit 12 is set in the sample immobilizing device 10. A pipette couple 19 is included in the sample immobilizing device 10, and has dispensing and removing pipettes 19a and 19b. The pipette 19a is set at the entrance liquid orifice 16a. The pipette 19b is set at the exit liquid orifice 16b. The pipette 19a introduces liquid to the flow channel 16. The pipette 19b sucks and removes liquid from the flow channel 16. The introduction with the pipette 19a is at the same time as the removal with the pipette 19b. Ligand solution or ligand liquid 21, as a liquid which contains ligand or biomolecule and liquid medium, is introduced through the entrance liquid orifice 16a by the pipette couple 19.

A linker film 22 is overlaid on a middle portion of the sensing surface 13a for binding with the ligand. In the manufacturing process of the sensor unit 12, the linker film 22 is formed. As the linker film 22 is a basis for immobilizing the ligand, a material for the linker film 22 is selectively determined.

Pre-treatment before immobilization with the ligand liquid 21 is wetting of the linker film 22 by use of liquid buffer, and activation of the linker film 22 for the purpose of facilitating binding of the ligand to the linker film 22. An example of a method is the amine coupling method. An example of material for the linker film 22 is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). After the activation, liquid buffer for immobilization is introduced to wash and clean the flow channel 16.

Various liquids are available for use as the liquid buffer for immobilization, and solvent or diluent for the ligand liquid 21. Examples of the liquids include buffer liquids, or physiological saline water and other aqueous solutions of physiological salts, and pure water. It is possible according to a type of a ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the linker film 22.

After the activation and washing, the ligand liquid 21 is introduced to the sensor cells 17 for a ligand immobilizing process. Ligand or sample 21a such as biomolecule diffused in the ligand liquid 21, in introducing the ligand liquid 21, gradually comes near to the linker film 22 and binds with the linker film 22. This is immobilization of the ligand 21a on the sensing surface 13a. It is general that a step of the immobilization requires approximately one (1) hour, during which the sensor unit 12 is preserved in an environment conditioned suitably, for example at a conditioned temperature. In the course of the immobilization, the ligand liquid 21 in the flow channel 16 may be left to stand in a stationary state. However, the ligand liquid 21 can be preferably stirred or turbulently flowed and kept fluid in the flow channel 16. The stirring or turbulent flow can promote binding of the ligand 21a with the linker film 22, to raise an immobilized amount of the ligand 21a.

When the immobilization of the ligand 21a on the sensing surface 13a is completed, then the ligand liquid 21 is removed from the flow channel 16. The pipette 19b discharges the ligand liquid 21 by suction. After this, the sensing surface 13a is washed by feeding washing liquid into the flow channel 16. A blocking step, if required, is added after the washing. A blocking liquid is introduced into the flow channel 16, to render inactive the reaction group remaining without binding with the ligand. A preferable example of the blocking liquid is ethanol amine hydrochloride. After the blocking, the flow channel 16 is washed again. Then evaporation retardant is introduced to the flow channel 16, which will be described in detail later. The sensor unit 12 is kept preserved until the assay with the sensing surface 13a contacting the evaporation retardant.

For the assay process, the sensor unit 12 is set in the assay apparatus 11. A pipette couple 26 is disposed in the assay apparatus 11 in the same manner as the pipette couple 19 in the sample immobilizing device 10. The pipette couple 26 introduces liquid of several types into the flow channel 16 through the entrance liquid orifice 16a. At first, liquid buffer for assay is introduced into the flow channel 16. After this, analyte solution or analyte liquid 27 as a liquid which contains analyte and liquid medium, is introduced into the flow channel 16. Again, the liquid buffer is introduced after the analyte liquid 27. Note that the flow channel 16 may be cleaned or washed before initially introducing the liquid buffer. Reading of data starts upon initially introducing the liquid buffer in order to detect a reference level of a signal. The reading is continued until the introduction of the liquid buffer at the second time after entry of the analyte liquid 27. It is possible not only to detect the reference level but to assay reaction or binding between the analyte and the ligand, and to measure a signal until release between the analyte and ligand in response to introduction of the liquid buffer.

There are a reaction region (act) and a reference region (ref) formed in the linker film 22. The reaction region has immobilization of a ligand, and is a region for reaction between the ligand and analyte. The reference region does not have immobilization of a ligand, and used for outputting a reference signal for comparison with a signal retrieved from the reaction region. Note that the reference region is formed in the course of film production of the linker film 22. An example of a process of the forming has steps of surface processing of the linker film 22 at first, and then rendering the reaction groups inactive in approximately a half of an entire area of the linker film 22 for binding with ligand. Thus, a half of the linker film 22 becomes the reaction region. A remaining half of the linker film 22 becomes the reference region.

An act-signal and ref-signal generated from those regions are measured simultaneously in the course of a period starting upon detection of a reference level, and then reaction of binding, and ending upon releasing. Data analysis is effected by obtaining a difference or ratio of the act-signal and ref-signal. For example, the data analyzer 91 obtains data of a finite difference between the act-signal and ref-signal, and analyzes various items according to the finite difference. This makes it possible to cancel electric noise caused by external irregularities, such as individual specificity of sensor units or sensor cells, mechanical changes of the assay apparatus, temperature changes of the liquid, and the like. A signal with a high S/N ratio can be obtained.

Various liquids are available for use as the liquid buffer for assay, and solvent or diluent for the analyte liquid 27. Examples of the liquids include buffer liquids, or physiological saline water and other aqueous solutions of physiological salts, and pure water. It is possible according to a type of a ligand to determine suitably solution types and pH values of the solutions, and types of substances to be mixed, and their density. To facilitate dissolving of the analyte, dimethyl sulfoxide (DMSO) can be added to the physiological saline water. The use of the DMSO is reflected to a level of an output signal. The buffer for assay is used for detecting the reference level, as described above. If DMSO is contained in the solvent for the analyte, it is preferable to use buffer for assay at a DMSO density approximately equal to that of the solvent in the analyte.

In general, the analyte liquid 27 may be kept preserved for a long time, for example one year. It is likely that a difference occurs between an initial level and a current level of the DMSO density owing to a change with time. If assay with high precision is required, such a difference in the density is estimated according to the ref-signal level upon introducing the analyte liquid 27, so that measured data can be compensated for by DMSO density compensation. Compensation data for the DMSO density compensation is obtained before introducing the analyte liquid 27. A plurality of liquid buffers different in the DMSO density are introduced to the sensor cells 17. Amounts of changes in the levels of ref-signal and act-signal are evaluated so as to obtain the compensation data.

An optical measuring unit or optical assay unit 31 is disposed in the assay apparatus 11. An illuminator 32 and a photo detector 33 are included in the optical assay unit 31. The reaction between the ligand and analyte can be recognized as a change of a resonance angle, which is an angle of incidence of light received by the light entering surface. To this end, the illuminator 32 is caused to apply light to the light entrance surface 13b at various values of angles of incidence satisfying a condition of the total reflection. The illuminator 32 includes a light source device 34 and an illuminating optical system 36, which includes a condensing lens, a diffusing plate and a polarizer. A position and angle of the installation of those elements are so determined that an angle of incidence of the light satisfies the condition of the above total reflection.

Examples of the light source device 34 include one light emitting diode (LED), laser diode (LD), super luminescent diode (SLD), and other light emitting element. A single element is used as the light source device 34, and applies light to a single one of the sensor cells 17. If a plurality of the sensor cells 17 are assayed at the same time, light from the single element may be split to illuminate the sensor cells 17 together. Also, a plurality of elements as the light source device 34 may be arranged and associated with respectively the sensor cells 17. The diffusing plate diffuses light from the light source device 34, and suppresses onset of irregularity in the light amount. The polarizer allows only light of p-polarization to pass, the light of p-polarization creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed unequal by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the light entrance surface 13b without irregularity in the intensity.

The photo detector 33 receives light reflected by the light entrance surface 13b, and detects intensity of the light. Rays of light are incident upon the light entrance surface 13b at various angles. It follows that light is reflected by the light entrance surface 13b at various angles of reflection according to the angles of the incidence. If there is a change in the resonance angle according to interaction of the analyte and ligand, a reflection angle at which light is attenuated is changed, too. An example of the photo detector 33 is a CCD area sensor, which retrieves such a change in the reflection angle as a gradual change in the attenuating position of the reflected light by the a photo receptor surface. The photo detector 33 generates measured data which is information of reaction state, and sends the measured data to the data analyzer 91. The data analyzer 91, in the data analyzing process, analyzes the measured data from the assay apparatus 11, to retrieve a characteristic of the analyte.

Note that in FIG. 4, the illuminator 32 and the photo detector 33 in the optical assay unit 31 are positioned so that a direction of light projected and reflected between those intersects horizontally with a flowing direction of the flow channel 16 between the pipettes, which is unlike that structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with a flowing direction of the flow channel 16 between the pipettes.

Figure 2:
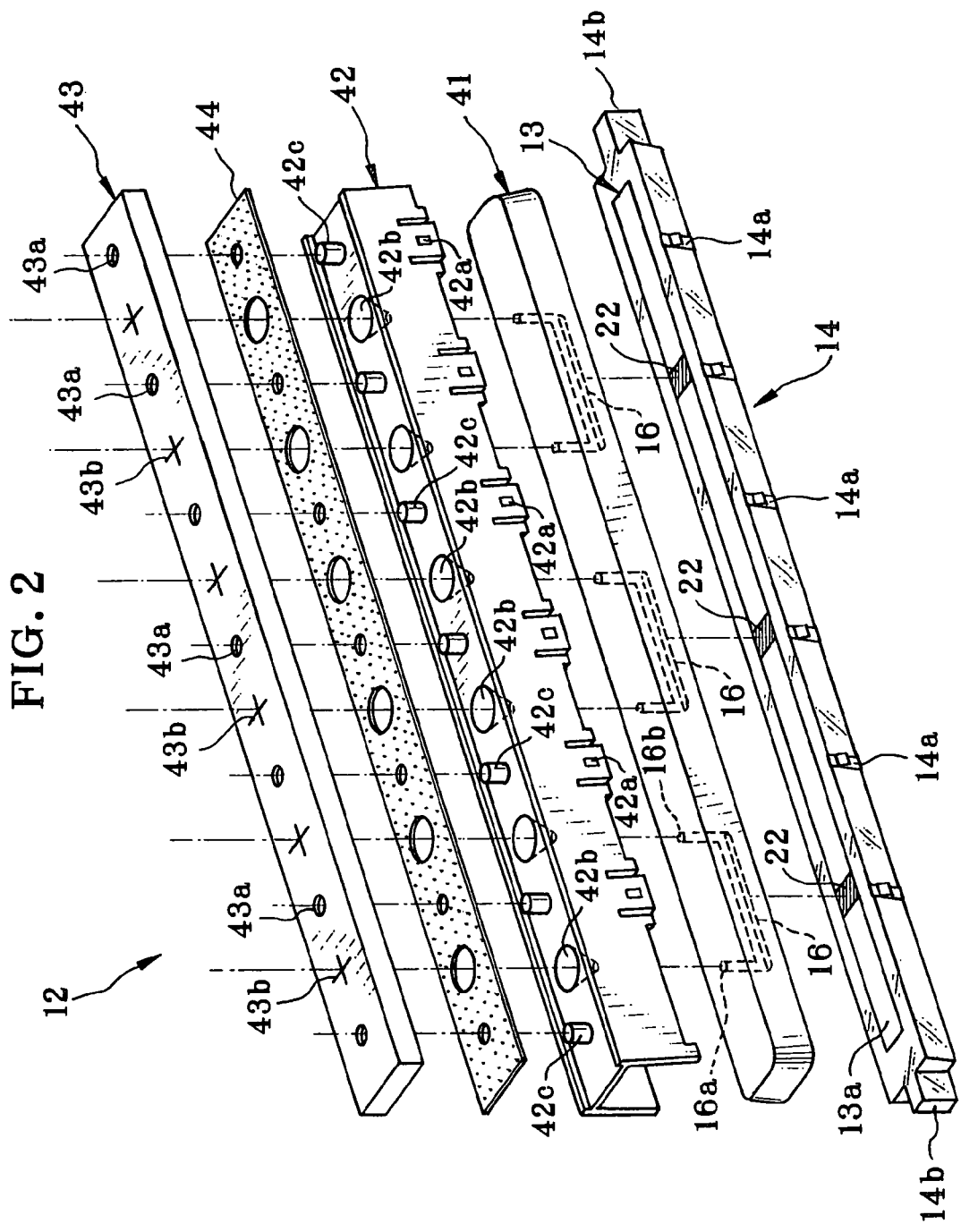
FIG. 2 is an exploded perspective view illustrating the sensor unit.

In FIG. 2, the sensor unit 12 is illustrated structurally. The sensor unit 12 includes a flow channel block 41, the prism 14, a retaining block 42, and a lid 43. The flow channel block 41 has the at least one flow channel 16 open therein. The prism 14 has the metal film 13 overlaid on its upper surface. The retaining block 42 supports the flow channel block 41 by fitting a lower surface of the flow channel block 41 on an upper surface of the prism 14. The lid 43 is disposed higher than the retaining block 42.

The flow channel 16, for example three (3) channels are formed in the flow channel block 41. The flow channel block-41 has a long shape, in which the flow channels 16 are arranged in a direction along the flow channel block 41. The flow channels 16 constitute the sensor cells 17 together with the metal film 13 in connection with its lower surface. See FIGS. 1A and 1B. The flow channel block 41 is formed from elastic material for the purpose of ensuring tightness in contact with the metal film 13. Examples of elastic materials includes rubber, polydimethylsilicone (PDMS), and the like. When a lower surface of the flow channel block 41 is pressed on an upper surface of the prism 14, the flow channel block 41 is elastically deformed, to remove a space between its surface and the metal film 13. Open lower portions of the flow channels 16 are closed water-tightly by the upper surface of the prism 14. Note that the number of the flow channels 16 may not be three, but can be one or two, or four or more.

The metal film 13 is deposited on the prism 14 by vapor deposition. The metal film 13 is formed in plural regions of long quadrilaterals opposed to the flow channel 16 formed in the flow channel block 41. Also, the linker film 22 is overlaid on an upper face or the sensing surface 13a of the metal film 13 and in regions associated with the flow channels 16. Claws 14a are formed to project from the prism 14 at its sides as viewed longitudinally. Claws 42a of the retaining block 42 are engageable with the claws 14a. The flow channel block 41 is sandwiched between the retaining block 42 and the prism 14. A lower surface of the flow channel block 41 is kept fitted on the prism 14. A composite part as biosensor is obtained by unifying the flow channel block 41, the metal film 13 and the prism 14.

End projections 14b protrude from ends of the prism 14 as viewed in its longitudinal direction. A sensor holder 52 of FIG. 3 contains the sensor unit 12. As will be described later, the immobilization on the sensor unit 12 is effected while the sensor unit 12 is contained in the sensor holder 52. The end projections 14b are formed for positioning the sensor unit 12 in a contained state in the sensor holder 52 by engagement with the sensor holder 52.

A receiving orifice 42b is formed in the retaining block 42, and positioned at each of the entrance liquid orifice 16a and the exit liquid orifice 16b of the flow channel 16, for entry of an end of each of dispensing and removing pipettes 26a and 26b and the dispensing and removing pipettes 19a and 19b. The receiving orifice 42b has a frusto-conical shape for introducing liquid ejected by the pipettes toward the entrance liquid orifice 16a. When the retaining block 42 is retained on the prism 14 with the flow channel block 41, a lower side of the receiving orifice 42b is connected with the entrance liquid orifice 16a and the exit liquid orifice 16b, for communication of the receiving orifice 42b with the flow channel 16.

Cylindrically shaped bosses 42c are formed to project beside the receiving orifice 42b. Positioning holes 43a are formed in the lid 43. The bosses 42c are fitted in the positioning holes 43a, to position the lid 43 firmly. Double-sided tape 44 attaches the lid 43 to an upper surface of the retaining block 42. Note that suitable holes are formed in the double-sided tape 44 and associated with the receiving orifice 42b and the bosses 42c.

The lid 43 covers the receiving orifice 42b communicating to the flow channel 16, and prevents evaporation of liquid in the flow channel 16. The lid 43 is formed from rubber, elastomer, resin or other elastic material. A cross shaped slit 43b is formed in the lid 43 and positioned at each of the receiving orifice 42b. The lid 43 is required to cover the receiving orifice 42b in order to prevent liquid in the flow channel 16 from evaporation. However, no pipette can enter the receiving orifice 42b if covering of the lid 43 is complete. So the cross shaped slit 43b is formed to enable insertion of pipettes, and to close the receiving orifice 42b while no pipette is inserted. If a pipette is forcibly pressed into the cross shaped slit 43b, edges of the cross shaped slit 43b are elastically deformed, to allow receipt of the pipette by becoming open. See FIGS. 1A and 1B. When the pipette is externally pulled out of the cross shaped slit 43b, the cross shaped slit 43b elastically closes the receiving orifice 42b again by returning to its initial state.

Figure 3:
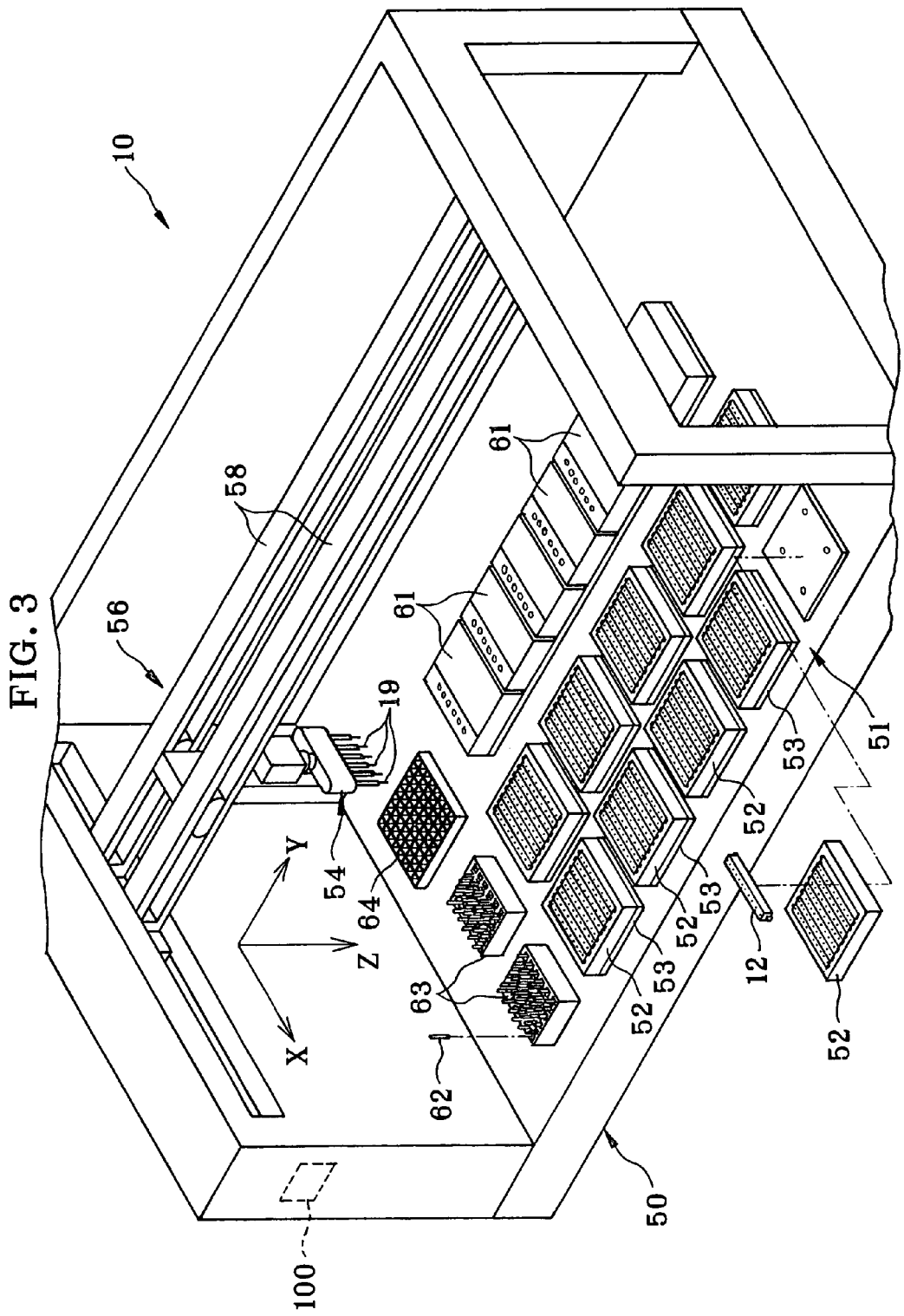
FIG. 3 is a perspective view, partially broken, illustrating the sample immobilizing device.

In FIG. 3, a casing base 50 is included in the sample immobilizing device 10. A setting space 51 as immobilizing stage of the sample immobilizing device 10 is formed on the casing base 50 so as to place the sensor unit 12 therein. While the setting space 51 contains the sensor unit 12, the entirety of the immobilizing process is effected. Thus, the setting space 51 constitutes the immobilizing stage for the sensor unit 12.

The sensor unit 12 is set in the sample immobilizing device 10 in a state contained in the sensor holder 52. For example, eight (8) of the sensor unit 12 can be contained in the sensor holder 52. The end projections 14b of the sensor unit 12 are engaged with engageable portions of the sensor holder 52, which positions the sensor unit 12. Also, a lower side of the sensor holder 52 is open except for a region for supporting ends of the sensor unit 12. If removal of the sensor unit 12 from the sensor holder 52 is desired in the assay process, the open side of the sensor holder 52 is accessed, as will be described later. A shifting element 81a of FIG. 4 is inserted in the open side, to push up the sensor unit 12.

The setting space 51 is so large that ten of the sensor holder 52 can be installed at one time there. Plural pallets 53 are disposed in the setting space 51. Positioning bosses are formed on each of the pallets 53 for positioning the sensor holder 52.

A pipetting head group 54 with a liquid transfer mechanism is disposed in the sample immobilizing device 10, and includes pipetting heads of the three pipette couples 19 for combination with pipette tips. The pipetting head group 54 accesses the sensor unit 12 in the setting space 51 to introduce and discharge liquid. As the pipette couples 19 are three pairs in the pipetting head group 54, three of the sensor cells 17 can be accessed in the sensor unit 12 for the introduction or discharge of liquid at the same time. A controller 100 is disposed in the sample immobilizing device 10, and controls the pipetting head group 54 for operation of the pipette couples 19 regarding various items, for example a amount of liquid in ejection or suction, and a time sequence of the ejection or suction.

A pipetting head moving assembly 56 on the casing base 50 moves the pipetting head group 54 in the three directions of X, Y and Z. An example of the pipetting head moving assembly 56 is constituted by elements including a transporting belt, pulley, carriage, motor and other well-known elements. The pipetting head moving assembly 56 includes a vertical shifter, a first horizontal shifter and a second horizontal shifter. The vertical shifter moves the pipetting head group 54 up and down. The first horizontal shifter includes guide rails 58, which keep the pipetting head group 54 movable in the direction Y together with the vertical shifter. The second horizontal shifter supports the guide rails 58 at two ends, and moves the pipetting head group 54 in the direction X together with the guide rails 58. The controller 100 controls the pipetting head moving assembly 56, and controls the vertical position and horizontal position of the pipetting head group 54 by driving the pipetting head moving assembly 56.

Plural liquid reservoirs 61 are disposed on the casing base 50 for storing various liquids to be supplied to the flow channel 16, the liquids including ligand liquid, washing liquid, liquid buffer for immobilization, evaporation retardant or evaporation inhibitor 70, activating liquid, blocking liquid and the like. The number of the liquid reservoirs 61 is determined according to the number of the types of liquid in use. Six insertion orifices are formed in the liquid reservoirs 61. The number and interval of the orifices are determined according to the number of pipettes associated with the pipetting head group 54 and their interval. The pipetting head group 54, for introduction of the liquid into the sensor cells 17, accesses the liquid reservoirs 61 to suck liquid, and then moves to the setting space 51 for introduction to the sensor unit 12.

A pipette tip tray or rack 63 is placed on the casing base 50. Pipette tips 62 are preserved in the pipette tip tray 63. The pipette tips 62 are fitted on ends of pipetting heads of the dispensing and removing pipettes 19a and 19b in a removable manner. As the pipette tips 62 comes in direct contact with liquid, the pipette tips 62 are exchanged for respective types of liquids in use so as not to prevent mixture or contamination of the liquids. Each of the dispensing and removing pipettes 19a and 19b is composite pipette equipment, which has a mechanism for automatically picking up and releasing the pipette tips 62 so as to renew the pipette tips 62 without manual operation. If renewal of the pipette tips 62 is desired, at first the pipetting head group 54 releases a used one of the pipette tips 62 by use of an abandoning unit (not shown). Then the pipetting head group 54 accesses the pipette tip tray 63 to pick up unused ones of the pipette tips 62.

There is a well plate 64 having a plurality of wells arranged in a matrix form. The well plate 64 is used for storing liquid retrieved by the pipettes in a preliminary manner, and also for mixing a plurality of liquids to prepare liquid composition.

For the immobilization, the casing of the sample immobilizing device 10 is covered by a cover (not shown), which intercepts the inside of the sample immobilizing device 10 and the setting space 51 from the outside. A temperature adjuster (not shown) keeps the temperature of the inside of the sample immobilizing device 10 adjustable. The sensor unit 12 remains set on the setting space 51 for a certain time after introduction of ligand on the sensor cells 17 and before completing the immobilization of the ligand 21a on the sensing surface 13a. In the course of preservation, the ligand liquid 21 is stirred or turbulently flowed in the flow channel 16 if required. The extent of immobilization depends upon temperature or other environmental conditions of the sensor unit 12. Thus, a temperature adjuster is used to keep the inside of the sample immobilizing device 10 at a predetermined temperature. The temperature and time for keeping the sample immobilizing device 10 are suitably determined according to a type of the ligand 21a.

When the immobilization is completed, liquid buffer is introduced as washing liquid. While the sensor cells 17 are filled with the ligand solution or ligand liquid as a liquid which contains ligand and liquid medium, the pipette 19a with the liquid buffer is inserted in the cross shaped slit 43b to introduce the liquid buffer to the sensor cells 17. When the liquid buffer is ejected from the entrance liquid orifice 16a to flow into the flow channel 16, the ligand liquid having been filled in the flow channel 16 is pressurized toward the exit liquid orifice 16b, and discharged from the flow channel 16. The pipette 19b is controlled for suction in synchronism with the pipette 19a in the dispensation. The pipette 19b retrieves the ligand liquid by suction at the same time as the supply of the liquid buffer. As a result, what is filled in the sensor cells 17 is changed over.

After completion of washing, evaporation retardant for the ligand 21a is introduced to the sensor cells 17 in the same manner as above. The liquid buffer is removed by substitution of the evaporation retardant. The sensor unit 12 after the substitution is transferred to the assay apparatus 11 together with the sensor holder 52 while the sensing surface 13a with the ligand 21a is wetted by the evaporation retardant. The ligand 21a can be prevented from drying before the start of the measurement.

Various liquids are available for use as the evaporation retardant 70. Examples of the evaporation retardant 70 include buffer liquids, or physiological saline water and other aqueous solutions of physiological salts, and pure water. It is possible according to a type of a ligand to determine suitably solution types and pH values of the solutions, and types of substances to be mixed, and their density. An amount of the evaporation retardant 70 is sufficient when the ligand 21a of the sensing surface 13a is wetted at all with the evaporation retardant 70 because drying of the ligand 21a can be prevented. However, it is preferable to use a greater amount than enough to wet the ligand 21a, for example to fill the flow channel 16 with the evaporation retardant 70, which is in consideration of reduction of the evaporation retardant 70 by evaporation of itself.

In FIG. 4, the assay apparatus 11 includes a holder moving mechanism 71, a pickup mechanism 72, a pipetting head moving assembly 73, and an assay stage 74. A casing 75 of the assay apparatus 11 accommodates those elements. The holder moving mechanism 71 includes a transporting belt 76, a carriage 77 and a pallet 78. The carriage 77 is secured on the transporting belt 76. The pallet 78 is secured to the carriage 77, and supports the sensor holder 52 containing the sensor unit 12 after the immobilization. The holder moving mechanism 71 shifts the pallet 78 in the direction X together with the sensor holder 52, to set each of the sensor units 12 to a pickup position for the pickup mechanism 72 to pick up.

The pickup mechanism 72 picks up the sensor unit 12 from the sensor holder 52, and includes a pressing shifter 81 and a handling head or chuck 82. The pressing shifter 81 presses up the sensor unit 12 contained in the sensor holder 52. The handling head 82, when the sensor unit 12 is pressed up by the pressing shifter 81, squeezes and holds the sensor unit 12. A middle of the sensor holder 52 has a holder opening. A middle of the support panel or pallet 78 has an opening associated with the holder opening. The pressing shifter 81 includes the shifting element 81a and a shifter driver 81b. The shifting element 81a moves from a lower side of the pallet 78 and upwards to come through the pallet 78, and contacts a lower surface of the sensor unit 12 by entry through the sensor holder 52 to push up the sensor unit 12. The shifter driver 81b drives the shifting element 81a to move up and down.

The handling head or chuck 82 includes two segments for squeezing or grasping the sensor unit 12 between those. A head body or chuck body 82a is a base of the handling head 82. A ball screw 86 in a sensor moving mechanism extends beside the handling head 82. A nut 84 between the handling head 82 and the ball screw 86 keeps the handling head 82 slidable in response to rotations of the ball screw 86. The handling head 82 is movable between a pickup position directly higher than the pallets 53, and a position at the measuring stage or assay stage 74. The handling head 82 when in the pickup position captures the sensor unit 12, moves in the direction Y, and transfers the sensor unit 12 to the assay stage 74. After the assay, the handling head 82 moves back to the pickup position, to release the sensor unit 12 being used at the pallets 53, to return the sensor unit 12 to the pallets 53.

In the assay stage 74 are disposed the illuminator 32 and the photo detector 33 under a level where the sensor unit 12 is disposed. The assay is made for each of the sensor cells 17 in the sensor unit 12. The sensor unit 12 is moved in the direction Y by an amount of the pitch of arrangement of the sensor cells 17, which is moved sequentially to an assay position located on a light path of the illuminator 32.

As has been described above, the illuminator 32 and the photo detector 33 are positioned so that a traveling direction of light between those intersects horizontally with the flow of the flow channel 16, namely the direction of arrangement of the sensor cells 17.

A well plate or liquid reservoirs 88 is placed beside the assay stage 74, for storing the analyte liquid 27. Plural types of the analyte liquid 27 different from one another are contained in the wells or liquid reservoirs 88. Note that the assay apparatus 11 includes a well plate (not shown), and a pipette tip tray or rack, both in positions easily accessed by the pipette couple 26. The well plate contains liquid buffer 80 for assay, and washing liquid. The pipette tip tray or rack contains pipette tips for renewal.

A pipetting head group 87 with a liquid transfer mechanism is constituted by the pipette couple 26. The pipetting head moving assembly 73 shifts the pipetting head group 87 in three dimensions of directions X, Y and Z, and positions the pipetting head group 87 selectively to the sensor unit 12 and the liquid reservoirs 88. The pipetting head moving assembly 73 is structurally the same as the pipetting head moving assembly 56 in the sample immobilizing device 10. The pipetting head group 87 accesses the sensor unit 12 to be measured, and introduces and removes liquids. The pipette couple 26 is only one pair of pipettes unlike the pipetting head group 54 in the sample immobilizing device 10, because only a particular one of the sensor cells 17 is accessed by the pipetting head group 87.

For an assay, the pipetting head group 87 accesses the well plate or liquid reservoirs 88 and sucks the analyte liquid 27 of a target type, and then moves to the assay stage 74 to supply one of the sensor cells 17 with the analyte liquid 27 in the assay position. The sensor unit 12 sent out of the sample immobilizing device 10 continues containing the evaporation retardant 70 in the sensor cells 17 until the onset of assay in a state mounted in the assay apparatus 11. Note that the evaporation retardant 70, upon introduction of the liquid buffer 80 for the assay, is pressurized and discharged from the sensor cells 17 by the liquid buffer 80, and sucked by the pipette 19b.

It is preferable to introduce the liquid buffer 80 at plural times in order to remove the evaporation retardant 70. If the liquid buffer 80 is introduced only at one time, failure is likely to occur in complete removal of the evaporation retardant 70 from the flow channel 16. Remainder of the evaporation retardant 70 may occur in the flow channel 16. However, a greater number of times of introducing the liquid buffer 80 is effective in ensured removal of the evaporation retardant 70. Should a part of the evaporation retardant 70 remain, an amount of the remainder can be minimized.

Measured data of the assay read by the photo detector 33 is transmitted to the data analyzer 91 by a communication interface. The data analyzer 91 obtains a result of assaying the reaction of the analyte and the ligand according to the measured data.

The operation of the above construction is described by referring to FIGS. 5 and 5A-5D. In the immobilizing process, the sensor unit 12 is placed in the setting space 51 of the sample immobilizing device 10 in a state contained in the sensor holder 52. At first, buffer for immobilization is introduced into each of the sensor cells 17, to wet the sensing surface 13a. Then activating liquid is introduced to activate the sensing surface 13a. After washing, the ligand liquid 21 is introduced into the sensor cells 17, to start immobilization. The sensor unit 12 is preserved and left to stand on the setting space 51. In the course of this, the ligand 21a in the solution binds with the linker film 22, and becomes immobilized.

The immobilization finishes upon a lapse of the prescribed time. A blocking process is effected after the washing. After the blocking process, the sensor cells 17 is washed again. Then the evaporation retardant 70 is introduced to the sensor cells 17. The sensor unit 12 is set in the pallet 78 in the assay apparatus 11 in a state contained in the sensor holder 52. When a command signal of starting assay is sent to the assay apparatus 11, the holder moving mechanism 71 is actuated to move the pallet 78, to shift a first one of the sensor unit 12 to the pickup position. The sensor unit 12 in the pickup position is picked up by the handling head 82, and transferred to the assay stage 74.

The sensor unit 12 transported to the assay stage 74 is moved in the direction Y. A specific one of the sensor cells 17 is set in an assay position to be measured. After this, the liquid buffer 80 is introduced into the sensor cells 17, to remove the evaporation retardant 70 by pressure. In response to the introduction of the liquid buffer 80, the optical assay unit 31 is driven and starts reading data. Then the analyte liquid 27 is introduced. When the analyte liquid 27 contacts the sensing surface 13a, reaction of the ligand with the analyte starts. At a lapse of a prescribed time, the liquid buffer 80 is introduced to remove the analyte liquid 27. After this, reading of data is completed. The measured data is transferred by the photo detector 33 to the data analyzer 91, and analyzed. This assay process is effected for the sensor cells 17 cell after cell.

In conclusion, the evaporation retardant 70 can be preserved in the sensor cells 17 after the immobilization because of the use of the sensor unit 12 including the flow channel 16 and the sensing surface 13a. The sensor unit 12 can be mounted in the assay apparatus 11 while the sensing surface 13a remains wetted with the evaporation retardant 70. The sensing surface 13a can be kept moist until assay after the immobilization no manner how long time passes between the immobilization and the assay. No drying of the ligand will occur. The assay can be free from failure due to drying, because no degradation of the ligand with time occurs, or because no long waiting time due to drying is required before becoming stable of an output signal of the biosensor. Note that a plurality of the sensor unit 12 can be handled together for sample immobilization at the same time according to the invention. It is possible to set and assay the sensor unit 12 in the assay apparatus 11 after the immobilization. This is effective in raising the throughput of the assay.

To remove the evaporation retardant, the liquid buffer is used to cause the same to flow out of the channel. So drying of the sensing surface 13a can be suppressed or minimized. Note that the lid at the sensor unit and having the cross-shaped slit also suppresses escapement of the evaporation retardant. The shape of the slit in the lid can be a form other than the cross shape, for example a line segment shape of a minus sign. Also, the lid may be shaped in various forms. Plural examples of shapes of lids are disclosed in CA-A 2,215,561 (corresponding to JP-A 10-150975).

In the above embodiment, the sensor unit includes the three sensor cells. However, the number of the sensor cells can be two, or four or more. Furthermore, sensor cells can be arranged in a matrix form, namely two or more arrays. Various modifications are possible according to the structure of the assay apparatus. U.S. Pat. No. 5,725,831 (corresponding to JP-A 7-265100) discloses a form of a sensor unit having one sensor cell.

In the above embodiment, the sensor unit is a composite structure including the metal film, flow channel and prism. However, no prism may be included in a sensor unit. Instead, a prism can be included in a main unit of the assay apparatus.

Also, a second evaporation retardant may be additionally used. In the above embodiment, not extremely long time passes before the assay after the immobilization. In contrast, much longer time is likely to pass until the assay according to a certain situation. For this, the second evaporation retardant is introduced in place of the evaporation retardant 70 initially introduced, to substitute the liquid. Furthermore, it is likely that volatilization of the evaporation retardant 70 is typically quick according to a certain condition. It is possible to add the evaporation retardant 70 as a surplus amount.

In the above embodiment, the buffer liquid is discharged by forcibly introducing the evaporation retardant with pressure as substitution of the buffer liquid for the evaporation retardant. However, other methods can be used. For example, the flow channel 16 can be emptied by suction and removal of the evaporation retardant, before the evaporation retardant can be introduced into the flow channel 16.

In the above embodiment, the casing of the assay apparatus having the assay stage is separate from the casing of the immobilizing device having the immobilizing stage. However, a single casing can be used to contain the immobilizing device and the assay apparatus, of which the immobilizing stage is still separate from the assay stage.

In addition to the SPR sensor, an assay sensor according to the invention can be other sensor in utilizing attenuated total reflection. One example of sensor according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a light entrance surface on the cladding layer. When light enters the light entrance surface to satisfy the condition of the total reflection, part of the light passes through the cladding layer, and enters the optical waveguide layer. A guided mode to propagate light is excited responsively in the optical waveguide layer, to attenuate the reflected light on the light entrance surface. An angle of the incidence at which the guided mode is excited is changeable according to the refraction index of the medium positioned on the sensing surface. This is similar to the characteristic of the resonance angle of the SPR sensor. The attenuation of the reflected light is detected, so that it possible to measure a state of reaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay method in utilizing attenuated total reflection by use of at least one sensor unit and an optical assay unit, wherein said sensor unit includes a transparent dielectric medium, and thin film having a light entrance surface and a sensing surface reverse to said light entrance surface, said light entrance surface being an interface in connection with said dielectric medium, and said sensing surface causing interaction between ligand of ligand liquid and analyte liquid, wherein said optical assay unit applies illuminating light through said dielectric medium to said light entrance surface in such a form as to satisfy a condition of total reflection, and assays interaction between said ligand and said analyte liquid by detecting attenuation of said illuminating light reflected by said light entrance surface, said assay method comprising:
   wherein said sensor unit includes a flow channel block having a flow channel for causing said ligand liquid and said analyte liquid to flow to said sensing surface;
   a step of, in an immobilizing stage, immobilizing said ligand on said sensing surface by introducing said ligand liquid to said flow channel for a prescribed period of time;
   a step of introducing evaporation retardant to said flow channel, for preventing drying of said immobilized ligand;
   a step of removing said evaporation retardant from said flow channel after transfer of said sensor unit from said immobilizing stage to an assay stage; and
   a step of introducing said analyte liquid to said flow channel, to assay said interaction.

2. An assay method as defined in claim 1, wherein said at least one sensor unit comprises plural sensor units, and said immobilizing step and said retardant introducing step are conducted for said plural sensor units together with one another in said immobilizing stage; thereafter, said sensor units are provided to said assay stage discretely, to conduct said retardant removing step and said assaying step.

3. An assay method as defined in claim 1, wherein said flow channel keeps said evaporation retardant contained after introduction thereof and until setting on said assay stage.

4. An assay method as defined in claim 1, wherein in said assay stage, additional liquid is introduced to said flow channel with said evaporation retardant left to stand therein, and said additional liquid is caused to discharge said evaporation retardant from said flow channel by substitution.

5. An assay method as defined in claim 4, wherein said additional liquid is buffer.

6. An assay method as defined in claim 1, wherein said evaporation retardant comprises any one of liquid buffer, solution of a physiological salt, and pure water.

7. An assay method as defined in claim 1, wherein said sensor unit includes:
   a lid for covering liquid orifices at ends of said flow channel;
   slits, formed in said lid, positioned at said liquid orifices, for being pushed open resiliently with deformation;
   wherein a pipette is used in at least one of said retardant introducing step and said retardant removing step by insertion in said slits.

8. An assay method as defined in claim 1, further comprising a step of, in said immobilizing stage, introducing washing buffer to said flow channel after immobilizing by introducing said ligand liquid and before introduction of said evaporation retardant.

9. An assay method as defined in claim 1, further comprising a step of introducing blocking liquid for blocking to said flow channel after immobilizing by introducing said ligand liquid and before introduction of said evaporation retardant.

10. An assay method as defined in claim 1, wherein said thin film is metal film, and said sensor unit comprises a surface plasmon resonance sensor for generating surface plasmon resonance on said sensing surface.

* * * * *